(12) United States Patent
Sugano

(10) Patent No.: US 6,861,260 B2
(45) Date of Patent: Mar. 1, 2005

(54) LIPID MEMBRANE, METHOD FOR MEASURING MEMBRANE PERMEABILITY, AND METHOD FOR SCREENING

(75) Inventor: Kiyohiko Sugano, Gotenba (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 124 days.

(21) Appl. No.: 10/239,522

(22) PCT Filed: Mar. 23, 2001

(86) PCT No.: PCT/JP01/02346

§ 371 (c)(1),
(2), (4) Date: Sep. 23, 2002

(87) PCT Pub. No.: WO01/70380

PCT Pub. Date: Sep. 27, 2001

(65) Prior Publication Data

US 2003/0111406 A1 Jun. 19, 2003

(30) Foreign Application Priority Data

Mar. 23, 2000 (JP) .................................. 2000-082177
Jun. 20, 2000 (JP) .................................. 2000-184973

(51) Int. Cl.$^7$ ............................................ G01N 30/00
(52) U.S. Cl. ............... 436/13; 204/403.08; 210/500.27; 422/61; 435/4; 435/287.1
(58) Field of Search ................................ 210/634, 639, 210/643–651, 500.21, 500.27, 500.28, 500.36; 204/403.07, 403.08; 435/4, 6, 7.1, 287.1, 287.3; 96/4; 422/61, 101; 585/601; 436/13, 17, 514, 518, 519, 528, 829; 424/450

(56) References Cited

U.S. PATENT DOCUMENTS

| | | | | |
|---|---|---|---|---|
| 4,490,216 A | * | 12/1984 | McConnell | 205/777.5 |
| 4,637,861 A | * | 1/1987 | Krull et al. | 205/782.5 |
| 4,758,342 A | * | 7/1988 | Heckmann et al. | 210/490 |
| 4,962,022 A | * | 10/1990 | Fleming et al. | 435/7.1 |
| 5,141,751 A | * | 8/1992 | Tomikawa et al. | 424/450 |
| 6,019,998 A | * | 2/2000 | Nomoto et al. | 424/450 |
| 6,177,700 B1 | * | 1/2001 | Lee | 257/306 |
| 6,451,543 B1 | * | 9/2002 | Kochendoerfer et al. | 435/7.1 |

FOREIGN PATENT DOCUMENTS

| JP | EP 0 344 807 | 12/1989 |
|---|---|---|
| JP | 8-173780 | 7/1996 |
| JP | 11-90214 | 4/1999 |

OTHER PUBLICATIONS

Kansy et al. "Physicochemical High Throughput Screening: Parallel Artificial Membrane Permeation Assay in the Description of Passive Absorption Processes" *Journal of Medicinal Chemsitry* (1998) 41(7); 3.

Inui et al. "Black Lipid Membranes as a Model for Intestinal Absorption FO Drugs" *Journal of Pharmacy and Pharmacology* (1977) 29: 22–26.

Thompson et al. "Structure and Electrochemical Properties of Microfiltration Filter–Lipid Membrane Systems" *Analytical Chemistry* (1982) 54: 76–81.

Xiang et al. "Substituent Contributions to the Transport of Substituted p–Toluic Acids Across Lipid Bilayer Membranes" *Journal of Pharmaceuitical Science* (1994) 83(10); 1511–1518.

Wessel et al. "Prediction of Human Intestinal Absorption FO Drug Compounds from Molecular Structure" *J. Chem. Inf. Comput. Sci* (1998) 38: 726–735.

Yazdanian et al. "Correlating Partitioning and CACO–2 Cell Permeability of Structurally Diverse Small Molecular Weight Compounds" *Pharmaceutical Research* (1998) 15(9): 1490–1494.

* cited by examiner

Primary Examiner—Joseph Drodge
(74) Attorney, Agent, or Firm—Browdy and Neimark, P.L.L.C.

(57) ABSTRACT

The object of the present invention is to provide a lipid membrane whose permeability to substances is high and strongly correlated with the permeability of biomembranes to drugs and which therefore is suitable for rapid measurement. The present invention provides a membrane comprising an unsaturated $C_7$–$C_9$ hydrocarbon and a lipid.

17 Claims, No Drawings

LIPID MEMBRANE, METHOD FOR MEASURING MEMBRANE PERMEABILITY, AND METHOD FOR SCREENING

This application is a 371 of PCT/JP01/02346, filed Mar. 23, 2001

TECHNICAL FIELD

The present invention relates to lipid membranes, more specifically lipid membranes that can be used for measuring the membrane permeability of substances.

BACKGROUND ART

Lipid membranes have heretofore been used as detection membranes or the like in sensors or measuring devices. For example, they have been used for the detection or assay of various substances such as metal ions, cyanide ions, alcohols and enzymes.

Lipid membranes have also been used for evaluating the permeability of biomembranes which mediate various reactions in the body, e.g., substance and/or energy transfer, metabolism, signal transduction, etc.

For example, the permeability of drugs across lipid membranes is closely related to gastrointestinal absorption and in vivo trans-tissue delivery of oral formulations, so it is a critical property in developing pharmaceuticals. In addition to drugs, it is also critical to evaluate the membrane permeability of substances which adversely affect living organisms (e.g., toxic substances, carcinogenic substances, etc.).

To determine the membrane permeability of substances in the body by an in vitro technique, there is a need to use a membrane whose permeability to substances is strongly correlated with the in vivo permeability of biomembranes to substances. In addition to this, throughput speed and cost are critical requirements for industrial application of such membranes. For example, when such a membrane is used to evaluate the membrane permeability of drugs in pharmaceutical development, the membrane is required to provide high throughput speed because a numerous number of compounds are required to be screened.

For in vitro determination of the membrane permeability of substances, several techniques are conventionally used, such as a technique using isolated organs, a technique using intestinal epithelium-derived cells, etc. However, because of their low throughput speed, these techniques are unable to provide rapid screening of a large number of substances.

Other techniques are also known for this purpose, e.g., an artificial membrane permeation assay using an artificial lipid membrane formed on a 96-well plate (see Manfred KANSY, Frank SENNER, Klaus GUBERNATOR; Journal of Medicinal Chemistry 1998, 41, 1007–1010). A lipid membrane prepared from a lipid(s) and an organic solvent(s) is used as an artificial lipid membrane in this technique. Major features of this technique include, for example, the ability to perform a parallel assay of many substances at the same time and low running cost due to the need to use only a small amount of substances for assay. However, the membrane used in the disclosed technique is disadvantageous in that it not only has a weak correlation with the in vivo permeability of biomembranes to substances, but it also involves difficulty in evaluating low-permeability substances and requires a long time for evaluation because the membrane is less permeable to substances.

Membranes used for measuring the membrane permeability of substances are known from, for example, Ken-ichi INUI, Katsue TABARA, Ryohei HIRI, Akemi KANEDA, Shozo MURANISHI, Hitoshi SEZAKI; Journal of Pharmacy and Pharmacology, 1977, 29, 22–26, which discloses a membrane that is prepared from living organism (rat) derived-membrane components dissolved in n-decane. This membrane is characterized by having a strong correlation with the permeability of biomembranes to substances, but it is still disadvantageous in that it involves difficulty in evaluating low-permeability substances and requires a long time for evaluation because the membrane is less permeable to substances.

Also, a membrane prepared from dodecane, phosphatidylcholine and 1,9-decadiene is known from Manfred KANSY, Frank SENNER, Klaus GUBERNATOR; Journal of Medicinal Chemistry 1998, 41, 1007–1010. However, such a membrane is similarly disadvantageous in that it requires a long time for measurement and involves difficulty in distinguishing between low-permeability substances because the membrane is less permeable to substances and a further disadvantage is in that it has a weak correlation with the permeability of biomembranes to substances.

DISCLOSURE OF THE INVENTION

As discussed above, conventional membranes used for measuring the membrane permeability of substances are disadvantageous in that they require a long time for measurement and involve difficulty in distinguishing between low-permeability substances because these membranes are less permeable to substances and that they have a weak correlation with the permeability of biomembranes to substances. The object of the present invention is to overcome these disadvantages and provide a lipid membrane whose permeability to substances is high and strongly correlated with the permeability of biomembranes to substances and which therefore is suitable for rapid measurement.

As a result of our careful studies, it has been found that the use of unsaturated $C_7$–$C_9$ hydrocarbons was effective in preparing a high-permeability lipid membrane suitable for rapid measurement, thereby finally completing one aspect of the invention.

We have further found that the use of unsaturated $C_7$–$C_9$ hydrocarbons and materials negatively charged at around neutral pH and/or lipids negatively charged at around neutral pH was effective in preparing a lipid membrane whose permeability to drugs was high and strongly correlated with the in vivo permeability of biomembranes to drugs and which therefore was suitable for rapid measurement; in this way, another aspect of the invention was finally completed.

Namely, the present invention provides a lipid membrane comprising an unsaturated $C_7$–$C_9$ hydrocarbon and a lipid.

Preferably, the lipid membrane further comprises a material negatively charged at around neutral pH. Alternatively, the lipid preferably is negatively charged at around neutral pH.

The unsaturated $C_7$–$C_9$ hydrocarbon preferably is heptadiene, octadiene or nonadiene, more preferably 1,6-heptadiene, 1,7-octadiene or 1,8-nonadiene.

The lipid membrane of the present invention may comprise one or more additional components, such as a carrier for transporting a specific substance (i.e., specific transporter).

The present invention also provides a method for measuring membrane permeability, which comprises the step of measuring the membrane permeability of a substance using the above-mentioned lipid membrane.

Further, the present invention provides a kit for measuring membrane permeability, which comprises an unsaturated $C_7$–$C_9$ hydrocarbon and a lipid. Such a kit may further comprise a support (e.g., a filter paper) capable of holding a lipid membrane prepared from an unsaturated $C_7$–$C_9$ hydrocarbon and a lipid.

The present invention provides a screening method, which comprises the steps of:

measuring the membrane permeability of a substance using the above-mentioned lipid membrane; and selecting the substance if it has the desired membrane permeability.

Further, the present invention provides a screening kit comprising an unsaturated $C_7$–$C_9$ hydrocarbon, a lipid and an instruction manual for use.

The measuring method of the present invention may also be combined with a method for determining membrane's active transport. A screening method comprising such combined methods and a screening kit used therefor are also included within the scope of the present invention.

The lipid membrane of the present invention not only evaluates the permeability of substances across biomembranes, but it can also be applied to sensors or measuring devices for chemical substances or the like.

BEST MODE FOR CARRYING OUT THE INVENTION

This application claims the priority of Japanese Patent Application Nos. 2000-82177 and 2000-184973, the disclosures of which are hereby incorporated by reference in their entirety.

The unsaturated $C_7$–$C_9$ hydrocarbon used herein may be linear or branched, examples of which include heptadiene, octadiene and nonadiene.

Examples of heptadiene include (Z)-1,3-heptadiene, (Z)-1,4-heptadiene, (Z)-1,5-heptadiene, 1,6-heptadiene, (E)-1,3-heptadiene, (E)-1,4-heptadiene, (E)-1,5-heptadiene, (2Z,4Z)-2,4-heptadiene, (2Z,5Z)-2,5-heptadiene, (2Z,4E)-2,4-heptadiene, (2Z,5E)-2,5-heptadiene, (2E,4Z)-2,4-heptadiene, (2E,5Z)-2,5-heptadiene, (2E,4E)-2,4-heptadiene, (2E,5E)-2,5-heptadiene, (3Z,5Z)-3,5-heptadiene, (3Z,5E)-3,5-heptadiene, (3E,5Z)-3,5-heptadiene and (3E,5E)-3,5-heptadiene, with 1,6-heptadiene being preferred.

Examples of octadiene include (Z)-1,3-octadiene, (Z)-1,4-octadiene, (Z)-1,5-octadiene, (Z)-1,6-octadiene, (E)-1,3-octadiene, (E)-1,4-octadiene, (E)-1,5-octadiene, (E)-1,6-octadiene, 1,7-octadiene, (2Z,4Z)-2,4-octadiene, (2Z,5Z)-2,5-octadiene, (2Z,6Z)-2,6-octadiene, (2Z,4E)-2,4-octadiene, (2Z,5E)-2,5-octadiene, (2Z,6E)-2,6-octadiene, (2E,4Z)-2,4-octadiene, (2E,5Z)-2,5-octadiene, (2E,6Z)-2,6-octadiene, (2E,4E)-2,4-octadiene, (2E,5E)-2,5-octadiene, (2E,6E)-2,6-octadiene, (3Z,5Z)-3,5-octadiene, (3Z,5E)-3,5-octadiene, (3E,5Z)-3,5-octadiene and (3E,5E)-3,5-octadiene, with 1,7-octadiene being preferred.

Examples of nonadiene include (Z)-1,3-nonadiene, (Z)-1,4-nonadiene, (Z)-1,5-nonadiene, (Z)-1,6-nonadiene, (Z)-1,7-nonadiene, (E)-1,3-nonadiene, (E)-1,4-nonadiene, (E)-1,5-nonadiene, (E)-1,6-nonadiene, (E)-1,7-nonadiene, 1,8-nonadiene, (2Z,4Z)-2,4-nonadiene, (2Z,5Z)-2,5-nonadiene, (2Z,6Z)-2,6-nonadiene, (2Z,7Z)-2,7-nonadiene, (2Z,4E)-2,4-nonadiene, (2Z,5E)-2,5-nonadiene, (2Z,6E)-2,6-nonadiene, (2Z,7E)-2,7-nonadiene, (2E,4Z)-2,4-nonadiene, (2E,5Z)-2,5-nonadiene, (2E,6Z)-2,6-nonadiene, (2E,7Z)-2,7-nonadiene, (2E,4E)-2,4-nonadiene, (2E,5E)-2,5-nonadiene, (2E,6E)-2,6-nonadiene, (2E,7E)-2,7-nonadiene, (3Z,5Z)-3,5-nonadiene, (3Z,6Z)-3,6-nonadiene, (3Z,5E)-3,5-nonadiene, (3Z,6E)-3,6-nonadiene, (3E,5Z)-3,5-nonadiene, (3E,6Z)-3,6-nonadiene, (3E,5E)-3,5-nonadiene and (3E,6E)-3,6-nonadiene, with 1,8-nonadiene being preferred.

These heptadiene, octadiene and nonadiene compounds may be used alone or in combination as an unsaturated $C_7$–$C_9$ hydrocarbon component. The lipid membrane of the present invention may comprise, as an organic solvent component, an unsaturated $C_7$–$C_9$ hydrocarbon either alone or in combination with other organic solvents.

Examples of the lipid used herein include saturated fatty acids, unsaturated fatty acids, phospholipids and cholesterols.

Saturated fatty acids include, but are not limited to, lauric acid, myristic acid, palmitic acid, stearic acid, arachidic acid and behenic acid.

Unsaturated fatty acids include, but are not limited to, palmitoleic acid, linolenic acid, linoleic acid, oleic acid and arachidonic acid.

Phospholipids include, but are not limited to, phosphatidylcholine, phosphatidylglycerol, phosphatidylinositol, phosphatidylserine, phosphatidylethanolamine and sphingomyelin.

These lipids may be used alone or in combination.

Examples of the material negatively charged at around neutral pH used herein include stearic acid, phosphatidylserine and phosphatidylinositol. These materials may be used alone or in combination.

The lipid membrane of the present invention preferably comprises the lipid and the unsaturated $C_7$–$C_9$ hydrocarbon at a ratio (i.e., lipid/unsaturated $C_7$–$C_9$ hydrocarbon ratio by weight) of 0.1% to 20%, more preferably 1% to 10%, and most preferably 1% to 2%.

In the case where the lipid membrane of the present invention comprises a material negatively charged at around neutral pH, the membrane preferably comprises the material in an amount of about 0.2 mmol/L to about 50 mmol/L, more preferably about 2 mmol/L to about 25 mmol/L, based on the sum of the lipid membrane components.

As used herein, the term "around neutral pH" generally refers to a range of pH 5.0 to pH 9.0, preferably pH 5.5 to pH 8.0, more preferably pH 6.0 to pH 7.5.

In addition, the term "negatively charged at around neutral pH" means that the material and/or lipid carries a negative charge in a given solvent at around neutral pH.

The lipid membrane of the present invention may further comprise one or more additional components other than those stated above. Such additional components may be selected as appropriate for the nature of substances, living organisms or tissues to be evaluated, etc. For example, the lipid membrane may comprise a carrier for transporting a specific substance (specific transporter).

The thickness of the lipid membrane of the present invention may be selected as appropriate for the nature of substances, living organisms or tissues to be evaluated, etc.

The lipid membrane of the present invention may be formed on a certain support. A preferred support is a porous sheet or film, such as filter paper. The support is preferably made of a hydrophobic material such as PTFE (polytetrafluoroethylene) or hydrophobic PVDF (polyvinylidene difluoride), more preferably hydrophobic PVDF. It is desirable to use a support with a pore size of 0.01 to 20 μm, preferably 0.05 to 10 μm, more preferably 0.1 to 5 μm, and most preferably around 0.1 to 1 μm.

Alternatively, the lipid membrane of the present invention may be formed so as to cover small pore openings having a diameter of about 0.5 to 2 mm, preferably around 1 mm.

The lipid membrane of the present invention can be prepared by mixing the above unsaturated $C_7$–$C_9$ hydrocarbon and the above lipid in a standard manner and then treated as described in Manfred KANSY, Frank SENNER, Klaus GUBERNATOR; Journal of Medicinal Chemistry 1998, 41, 1007–1010 or elsewhere.

The measuring method of the present invention comprises the step of measuring the membrane permeability of substances using the lipid membrane of the present invention. In this method, the lipid membrane to be used for measurement may be formed and stored prior to the measurement or it may be formed immediately before the measurement. The lipid membrane is preferably formed on a support, more preferably on a hydrophobic support. A solution containing a test substance is injected into one side (called "side A") of the resulting lipid membrane, while a solvent free of the test substance is injected into the other side (called "side B"). The solvent injected into side B is preferably identical with a solvent for the solution of the test substance injected into side A. After a given time period has passed, the amount of the test substance that has permeated across the lipid membrane from side A to side B is determined. Instead of direct measurement of the test substance that has permeated across the lipid membrane, the amount of the test substance remaining on side A (i.e., without permeating across the lipid membrane) may also be measured to calculate the amount of the test substance that has permeated across the lipid membrane.

The lipid membrane may be placed in any direction with respect to the gravity vector, for example, in a direction either parallel or perpendicular to the gravity vector. Also, the direction of substance permeation is not particularly limited. For example, the substance permeation may be set in a direction parallel, opposite or perpendicular to the gravity vector.

The measurement may be performed using a container divided by the lipid membrane into two compartments or using two separate containers, one of which is provided for a solution of the test substance and the other is provided for a solvent free of the test substance. For example, a combination of an upper cylindrical container having a filter at the bottom and a lower container having an open top can be used for measurement purposes. Preferably, the lower end of the upper container and the upper end of the lower container are of the same size. The lower container is filled with the solvent free of the test substance and the upper container is placed on the lower container. After the lipid membrane of the present invention is formed on the filter, the solution of the test substance is injected into the upper container and the amount of the test substance in the lower container is determined after a given time period has passed. The upper container is placed on the lower container such that the filter of the upper container contacts the solvent in the lower container. The upper and lower containers should be so fixed as to prevent fluid leakage from between the mating surfaces as they hold the filter. Rubber packing or the like may be used for this purpose. The filter is not always required to be attached to the bottom of the upper container.

In the case where rapid measurement of membrane permeability is performed on two or more test substances, it is desirable to use a multi-well plate, which may be used as a lower container. In this case, each well of the multi-well plate is filled with the solvent free of the test substance and then covered with a porous film such as filter paper. After an upper plate perforated with holes at positions corresponding to individual wells (used as an upper container) is placed on the multi-well plate, a lipid membrane is formed on the porous film within each hole, into which the solution of the test substance is then injected. Alternatively, the upper plate may have a filter at the bottom of each hole. For example, a chamber plate for chemotaxis assay or the like may be used.

In either of these cases, the solvent free of the test substance may be injected into the upper container, while the solution of the test substance may be injected into the lower container.

The amount of the substance that has permeated across the lipid membrane may be determined using, for example, absorbance measurement, HPLC, TLC (thin-layer chromatography), GC-MS (gas chromatography/mass spectrometry), LC-MS (liquid chromatography/mass spectrometry), fluorescence analysis, NMR, IR and CE (capillary electrophoresis), preferably absorbance measurement, HPLC and LC-MS.

In the present invention, as shown in the examples below, the membrane permeability of substances was measured as described in Manfred KANSY, Frank SENNER, Klaus GUBERNATOR; Journal of Medicinal Chemistry 1998, 41, 1007–1010. In addition to this, the measurement may be performed as described in, for example, Michael THOMPSON, R. Bruce LENNOX, R. A. MCCLELLAND, Analytical Chemistry, 1982, 54, 76–81 or Tian-xiang XIANG, Bradley D. ANDERSON, Journal of Pharmaceuitical Science, 1994, 83, 1511.

To perform screening of substances using the lipid membrane of the present invention, the membrane permeability of test substances is measured as stated above and test substances with the desired membrane permeability are then selected. In this screening, a certain reference substance may be used to select substances with higher or lower membrane permeability than the reference substance. Alternatively, test substances with the same membrane permeability as the reference substance may be selected.

The screening kit of the present invention, which is helpful in effecting such screening rapidly and conveniently, comprises an unsaturated $C_7$–$C_9$ hydrocarbon, a lipid and an instruction manual for use. In addition to these components, the kit may further comprise a support for the lipid membrane (e.g., filter paper, preferably a hydrophobic filter paper), a multi-well plate for use in measurement of membrane permeability, a solvent, a reference substance for evaluation of membrane permeability, a carrier for transporting a specific substance (specific transporter), a solvent for dissolving test substances, etc. Alternatively, the screening kit of the present invention may comprise a pre-formed lipid membrane instead of an unsaturated $C_7$–$C_9$ hydrocarbon and a lipid. Such a preformed lipid membrane may be on a support.

The present invention will be further described in the following examples. The examples are provided for illustrative purposes only, and are not intended to limit the scope of the invention. For example, various conditions including the thickness of a lipid membrane to be prepared, the concentration of lipid and the pH of a buffer can be adjusted as appropriate for the nature of substances, living organisms or tissues to be evaluated, etc.

EXAMPLES

Preparation of Lipid Membranes

Each well (volume: 360 µL) of a 96-well plate (flat-bottomed plate 3072, Falcon) was filled with a 50 mmol/L sodium phosphate buffer containing 5% dimethyl sulfoxide (pH 6.5 to pH 7.0; hereinafter referred to as "buffer") and the 96-well plate was then covered with a filter plate (Millipore Multiscreen filter plate, hydrophobic PVDF MAIPN4510; thickness: 0.45 µm). At that time, it was confirmed that there was no air bubble between the filter plate and the buffer in the 96-well plate. Each of the components shown in Table 1 (membrane composition) was dissolved in 1,7-octadiene in the amount also indicated in Table 1. The resulting 1,7-octadiene solution was added to the filter within each well in a volume of 4 to 5 µL per well to form a membrane on the filter (Examples 1 and 2).

Similarly, a solution containing phosphatidylcholine and 1,6-heptadiene (2:98) was added to the filter within each well in a volume of 4 to 5 µL per well to form a membrane on the filter (Example 3). A solution containing phosphatidylcholine and 1,7-octadiene (2:98) was added to the filter within each well in a volume of 4 to 5 µL per well to form a membrane on the filter (Example 4). A solution containing phosphatidylcholine and 1,8-nonadiene (2:98) was added to the filter within each well in a volume of 4 to 5 µL per well to form a membrane on the filter (Example 5).

In control experiments, a solution containing phosphatidylcholine, cholesterol and 1,9-decadiene (2:1:97) was prepared and added to the filter within each well in a volume of 4 to 5 µL per well to form a membrane on the filter (Comparative Example 1). A solution containing phosphatidylcholine and 1,9-decadiene (2:98) was added to the filter within each well in a volume of 4 to 5 µL per well to form a membrane on the filter (Comparative Example 2).

Measurement of Membrane Permeability

Each of the compounds shown in Tables 2 and 3 was dissolved in the buffer to give a 0.5 mmol/L solution, which was then used as a sample solution in a volume of 100 to 200 µL (volume of the sample solution added to each well: $V_{dn}$). The sample solutions thus prepared were added to individual wells where the membrane had been formed as stated above, followed by allowing them to stand for 2 to 15 hours (permeation time: t) with the plate covered with a lid. After the filter plate was removed, an aliquot (200 µL) was taken from each well of the lower 96-well plate and used as a test solution.

The resulting test solutions (200 µL each) were assayed for their absorbance ($OD_{ac}$) over the wavelength range from 250 to 450 nm at intervals of 10 to 20 nm. As a reference solution, the sample solution used in Example 1 or 3 was used on its own (undiluted reference solution) or diluted 4.8-fold (V/V) in the buffer (diluted reference solution). Namely, either the undiluted or the diluted reference solution was used in a volume of 200 µL and similarly assayed for its absorbance ($OD_{ref}$). The permeability coefficient was calculated according to the following equation:

Permeability coefficient $(P) = -2.30333 \, (V_{dn} \times V_{ac}/(V_{dn} \times V_{ac}))/(S \times t) \times \log(1-\text{flux }\%/100)$ where flux $\% = OD_{ac}/OD_{ref} \times A \times 100$ $OD_{ac}$: measured absorbance of the test solution
$OD_{ref}$: measured absorbance of the reference solution
$V_{ac}$: volume of each well in the lower plate (360 µL)
$V_{dn}$: volume of the sample solution added to each well (100 to 200 µL)
A: $V_{dn} \times V_{ac}$ (undiluted reference solution) or 1 (diluted reference solution)
S: area of the membrane (0.266 cm$^2$)
t: permeation time (sec).

Tables 2 and 3 show the calculated permeability coefficients (P) of individual compounds.

With respect to the membranes of Examples 1 and 2 and Comparative Example 1, the correlation coefficient (R) was further calculated using the following approximation curve obtained from human intestinal absorption (Fa) data of individual compounds, which were found in the following References *1 to *4:

Approximation curve: $Fa \, (\%) = (1 - \exp(-a \times P)) \times 100$ where
exp: exponential
a: coefficient.

References:

*1 Matthew D. Wessel et al., J. Chem. Inf. Comput. Sci., 38, 1998, 726–735
*2 Mehran Yazdanian et al., Pharm. Res., Vol. 15, No. 9, 1998, 1490–1494
*3 Gerald K. McEvoy, AHFS, 1998

TABLE 1

| | Phosphatidyl-choline (%, w/w) | Phosphatidyl-ethanolamine (%, w/w) | Phosphatidyl-serine (%, w/w) | Phosphatidyl-inositol (%, w/w) | Cholesterol (%, w/w) | Stearic acid (%, w/w) |
|---|---|---|---|---|---|---|
| Example 1 | 2 | 0 | 0 | 0 | 1 | 0.2 |
| Example 2 | 0.75 | 0.75 | 0.25 | 0.25 | 1 | 0 |

*4 Manfred Kansy et al., J. Med. Chem., Vol. 47, No. 7, 1998, 1007–1010

Table 2 also shows the calculated correlation coefficients (R) and human intestinal absorption (Fa) data of individual compounds.

TABLE 2

| Compound | Example 1 (P) pH 7.0 | Example 2 (P) pH 6.5 | Comparative Example 1 (P) pH 6.5 | Human intestinal absorption (Fa, %) |
|---|---|---|---|---|
| Acebutolol | 4.45E-06 | 3.67E-06 | 1.91E-07 | 90*1 |
| Acetaminophen | 8.17E-06 | 1.79E-06 | 4.98E-08 | 80*1 |
| Aciclovir | 7.97E-08 | 8.89E-08 | 3.87E-08 | 20*2 |
| Amiloride | 2.69E-06 | 6.73E-07 | 6.10E-08 | 50*3 |
| Atenolol | 8.02E-07 | 8.64E-07 | 4.18E-07 | 50*1 |
| Ceftriaxone | 1.37E-06 | 2.25E-07 | 1.66E-08 | 1*4 |
| Cefuroxime | 1.60E-07 | 4.43E-08 | 2.76E-08 | 5*1 |
| Chlorothiazide | 2.24E-06 | 2.71E-07 | 4.98E-08 | 13*1 |
| Cytarabine | 8.89E-07 | 3.87E-08 | 3.87E-08 | 20*3 |
| Doxycycline | 7.07E-06 | 2.35E-05 | 1.52E-06 | 95*3 |
| Enalapril | 8.02E-07 | 1.37E-06 | 1.09E-06 | 65*3 |

TABLE 2-continued

| Compound | Example 1 (P) pH 7.0 | Example 2 (P) pH 6.5 | Comparative Example 1 (P) pH 6.5 | Human intestinal absorption (Fa, %) |
|---|---|---|---|---|
| Furosemide | 3.09E-06 | 9.02E-07 | 1.34E-07 | 61[*1] |
| Guanabenz | 1.95E-05 | 1.04E-05 | 4.14E-06 | 75[*1] |
| Hydrochlorothiazide | 1.34E-06 | 1.55E-06 | 8.64E-07 | 67[*1] |
| Hydrocortisone | 8.84E-06 | 1.44E-05 | 3.18E-06 | 91[*1] |
| Metoprolol | 9.42E-06 | 6.88E-06 | 7.49E-07 | 95[*1] |
| Nadolol | 3.28E-06 | 1.14E-06 | 5.26E-07 | 35[*1] |
| Naltrexone | 1.12E-05 | 4.50E-06 | 9.61E-06 | 96[*3] |
| Oxytetracycline | 3.31E-06 | 5.87E-06 | 8.31E-07 | 60[*3] |
| Pindolol | 1.10E-05 | 7.94E-06 | 2.71E-08 | 90[*1] |
| Practolol | 1.01E-06 | 1.53E-06 | 4.36E-07 | 100[*1] |
| Pravastatin | 2.69E-06 | 6.12E-07 | 7.21E-08 | 34[*1] |
| Procainamide | 4.58E-06 | 3.89E-06 | 1.17E-07 | 85[*3] |
| Quinidine | 2.56E-05 | 1.47E-05 | 4.51E-06 | 80[*1] |
| Ranitidine | 1.22E-06 | 2.19E-06 | 1.34E-07 | 50[*1] |
| Sulfasalazine | 3.24E-06 | 1.07E-06 | 3.12E-07 | 65[*1] |
| Sulpiride | 1.34E-06 | 2.23E-06 | 8.33E-08 | 35[*4] |
| Tetracycline | 2.65E-06 | 7.62E-06 | 1.40E-06 | 77.5[*3] |
| Timolol | 9.13E-06 | 1.19E-05 | 1.05E-06 | 90[*1] |
| Correlation coefficient (R) between P and human intestinal absorption | 0.798 | 0.847 | 0.534 | — |

TABLE 3

| Compound | Example 3 (P) | Example 4 (P) | Example 5 (P) | Comparative Example 2 (P) |
|---|---|---|---|---|
| Hydrocortisone | 4.36E-05 | 1.87E-05 | 1.29E-05 | 1.75E-06 |
| Propranolol | 4.38E-05 | 2.15E-05 | 2.46E-05 | 1.25E-05 |
| Ketoprofen | 5.05E-05 | 1.36E-05 | 1.68E-05 | 9.22E-06 |
| Procainamide | 1.99E-06 | 2.42E-07 | 4.51E-07 | 3.14E-07 |
| Furosemide | 4.97E-06 | 1.66E-06 | 3.12E-06 | 2.44E-07 |
| Hydrochlorothiazide | 5.86E-06 | 1.52E-06 | 1.82E-06 | 7.51E-07 |

INDUSTRIAL APPLICABILITY

The present invention provides lipid membranes whose permeability to substances is high and strongly correlated with the permeability of biomembranes to substances and which therefore is suitable for rapid measurement. Such lipid membranes have great utility.

What is claimed is:

1. A lipid membrane comprising an unsaturated $C_7$–$C_9$ hydrocarbon and a lipid.

2. The lipid membrane according to claim 1, which further comprises a material negatively charged at around neutral pH.

3. The lipid membrane according to claim 2 wherein the unsaturated $C_7$–$C_9$ hydrocarbon is heptadine, octadine or nonadiene.

4. The lipid membrane according to claim 2 wherein the unsaturated $C_7$–$C_9$ hydrocarbon is 1,6-heptadiene, 1,7-octadiene or 1,8-nonadiene.

5. The lipid membrane according to claim 2, wherein the unsaturated $C_7$–$C_9$ hydrocarbon is heptadiene, octadiene, or nonadiene.

6. The lipid membrane according to claim 2, wherein the unsaturated $C_7$–$C_9$ hydrocarbon is 1,6-heptadiene, 1,7-octadiene, or 1,8-nonadiene.

7. The lipid membrane according to claim 1, wherein the lipid is negatively charged at around neutral pH.

8. The lipid membrane according to claim 7 wherein the unsaturated $C_7$–$C_9$ hydrocarbon is heptadiene, octadiene or nonadiene.

9. The lipid membrane according to claim 7 wherein the unsaturated $C_7$–$C_9$ hydrocarbon is 1,6-heptadiene, 1,7-octadiene or 1,8-nonadiene.

10. The lipid membrane according to claim 7, wherein the unsaturated $C_7$–$C_9$ hydrocarbon is heptadiene, octadiene, or nonadiene.

11. The lipid membrane according to claim 7, wherein the unsaturated $C_7$–$C_9$ hydrocarbon is 1,6-heptadiene, 1,7-octadiene, or 1,8-nonadiene.

12. The lipid membrane according to claim 1, wherein the unsaturated $C_7$–$C_9$ hydrocarbon is heptadiene, octadiene or nonadiene.

13. The lipid membrane according to claim 1, wherein the unsaturated $C_7$–$C_9$ hydrocarbon is 1,6-heptadiene, 1,7-octadiene or 1,8-nonadiene.

14. A method for measuring membrane permeability, which comprises the step of measuring the membrane permeability of a substance using the lipid membrane according to any one of claims 1 to 13.

15. A screening method, which comprises the steps of:
   measuring the membrane permeability of a substance using the lipid membrane according to any one of claims 1 to 13; and
   selecting the substance if it has the desired membrane permeability.

16. A kit for measuring membrane permeability, which comprises an unsaturated $C_7$–$C_9$ hydrocarbon and a lipid.

17. A screening kit comprising an unsaturated $C_7$–$C_9$ hydrocarbon, a lipid and an instruction manual for use.

* * * * *